United States Patent [19]

Wilkins

[11] Patent Number: 5,440,940

[45] Date of Patent: *Aug. 15, 1995

[54] PIPETTE-SYRINGE-TUBULAR MICROBIAL RETRIEVAL AND SAMPLER

[76] Inventor: Judd R. Wilkins, 281 Littletown Quarter, Williamsburg, Va. 23185

[ * ] Notice: The portion of the term of this patent subsequent to Dec. 28, 2010 has been disclaimed.

[21] Appl. No.: 210,277

[22] Filed: Mar. 18, 1994

[51] Int. Cl.$^6$ ............................................. G01N 1/14
[52] U.S. Cl. .................. 73/864.16; 422/100; 73/864.91
[58] Field of Search ........... 73/864.01, 864.11, 864.13, 73/864.14, 864.16, 864.17, 864.18, 864.91; 422/100

[56] References Cited

U.S. PATENT DOCUMENTS

| | | | |
|---|---|---|---|
| 3,732,734 | 5/1973 | Avakian | 73/864.14 |
| 3,991,617 | 11/1976 | d'Autry | 73/864.14 |
| 4,009,611 | 3/1977 | Koffer | 73/864.14 |
| 4,023,716 | 5/1977 | Shapiro | 73/864.13 |
| 4,151,750 | 5/1979 | Suovaniemi | 73/864.14 |
| 4,283,950 | 8/1981 | Tervamaki | 422/100 |
| 4,487,081 | 12/1984 | De Vaughn et al. | 73/864.16 |
| 4,662,545 | 5/1987 | Kenney | 73/864.13 |
| 5,249,711 | 10/1993 | Filbert, Jr. | 422/100 |
| 5,272,926 | 12/1993 | Wilkins | 73/864.13 |

FOREIGN PATENT DOCUMENTS 2203174 8/1973 Germany ........................ 73/864.16

*Primary Examiner*—Hezron E. Williams
*Assistant Examiner*—Nashmiya Ashraf
*Attorney, Agent, or Firm*—Wallace J. Nelson

[57] ABSTRACT

A pipette-syringe combination having a removable cover and employing a tubular sampling probe to take a bacterial sample from a culture includes a pipette cover provided over the pipette orifice and attached thereto via a stressed elastomeric strap. The cover is provided with an extension that permits manual grasping, removal, and replacement of the cover. After cover removal, the tip of the tubular sampling probe is syringe extended to contact a culture growth and retracted back within the pipette. A quantity of nutrient broth is added to the pipette, and the protective cover manually replaced to hermetically seal the nutrient broth and culture sample therein. The pipette is then incubated at the desired temperature and for the desired time. At least one transverse opening is provided through the sidewall of the tubular sampling probe for access of growth media to contact any sample retrieval within the lumen thereof. The tip end of the probe may be blunt or tapered and provided with a bevelled or tapered sidewall to form a sharp penetration end that works equally as well in obtaining samples from soft, solid or semi-solid materials.

13 Claims, 2 Drawing Sheets

5,440,940

PIPETTE-SYRINGE-TUBULAR MICROBIAL RETRIEVAL AND SAMPLER

CROSS-REFERENCE TO RELATED APPLICATION

This invention is an improvement of the invention disclosed in applicant's application Ser. No. 08/112,957 filed Aug. 30, 1993 (a division of Ser. No. 07/791,467 filed Nov. 13, 1991 and issued as U.S. Pat. No. 5,272,926 on Dec. 28, 1993), and the subject matter of which is incorporated herein by reference.

FIELD OF THE INVENTION

This invention relates generally to sampling devices and relates specifically to a pipette-syringe combination retrieval and sampling device employing a tubular sampling component and having a removable, protective cover disposed over the orifice thereof.

BACKGROUND OF THE INVENTION

It is an accepted and common procedure in a microbiology laboratory to spread a sample over a nutrient agar surface to obtain isolated colonies of growth. After incubation, a colony is selected for further studies and transferred to sterile nutrient broth. This transfer is normally accomplished by employing a straight wire or loop attached to a suitable handle, sterilized in a Bunsen burner, and cooled. A portion of the wire tip is touched or embedded within the colony and adhering bacterial cells released from the straight wire or loop by (1) inserting the wire in a tube of nutrient broth and vigorously flicking the wire from one side of the tube to the other, or (2) touching the wire or loop tip to the side of the tube and washing the cells off the tube wall with nutrient broth. Although previously not practical, in applicant's referenced prior application, the transfer straight wire was allowed to remain in the tube of nutrient broth during incubation.

The wire probe used to sample the colony in applicant's referenced prior invention acts very much like the previously employed straight or loop transfer wire in the laboratory. However, a major difference in applicant's system is that movement of cells adhering to the wire probe relies on the movement of broth over the probe by the pulling action of the plunger within the syringe barrel. Cells not freed by this action remain as a locus of growth at or near the tip of the pipette.

It is an object of the present invention to provide an improved pipette-syringe combination that can also serve as a growth chamber for the collected sample.

Another object of the present invention is an improved pipette-syringe sampling system that increases the efficiency of collecting, releasing, and dispersing cells within the pipette over that attained by a conventional wire or loop sampler.

An additional object of the present invention is an improved sampling probe that contacts and retains more of a bacterial culture growth than previously employed sampling probes.

A further object of the present invention is a process of obtaining a representative bacterial sample on and within a tubular sampling probe, positioning the sample containing probe in a pipette, adding and sealing a quantity of nutrient broth in the pipette, and incubating the sample in the nutrient broth containing pipette before transferring the accumulated culture growth to a number of tubes.

SUMMARY OF THE INVENTION

The foregoing and additional objects are attained, according to one aspect of the present invention, by providing a tubular sampling probe inside a conventional plastic pipette-syringe combination and securing the sampling probe to the bottom of the pipette plunger in the syringe. The length of the sampling probe is selected such that the unattached end thereof is maintained within the pipette when the plunger is retracted and is extended a controlled distance from the pipette sampling orifice when the plunger is fully depressed. The pipette-syringe combination is designed as a sterile disposable, or "one use only" unit.

By providing the sampling probe attached to the plunger, the movement of the probe inside the pipette is controlled by the pulling and pushing action of the plunger inside the barrel of the syringe. A removable plastic cap is disposed over the pipette orifice and has one edge surface thereof attached to the exterior of the pipette wall via an elastic strap. The downward motion of the sampling probe, responsive to pushing on the plunger, pushes the removable cap away from the pipette orifice and the elastic strap acting on the edge of the cap retracts the cap away from the pipette orifice. Alternatively, the removable cap may be manually removed from the end of the pipette.

The end of the tubular sampling probe extends from the pipette orifice sufficiently to permit contact, or sampling of, a surface colony of bacterial growth in a Petri dish, or the like. After contact, the tubular sampling probe is withdrawn back through the pipette orifice as the probe is retracted by an upward pull of the plunger. The tip of the pipette is then placed in nutrient broth and sterile media drawn into the pipette by the pulling action of the plunger-syringe barrel. The upward pull of the plunger simultaneously creates a suction force that forces the nutrient broth into the pipette. The orifice cover is then manually placed over the pipette tip for hermetically sealing of the pipette orifice and the entire pipette placed in an incubator for 18 to 24 hours at the desired temperature, usually 37° C.

One or more transverse openings are provided through the sidewall of the tubular sampling probe. These openings permit the nutrient broth placed in the pipette to flow interiorly of the tubular sampling probe and contact and promote growth of any of the sample that is received within the tubular cavity when a sample is taken of a colony growth. After incubation, the accumulated growth is uniformly distributed by a back-and-forth rocking motion of the pipette and, after manual removal of the orifice cover, the growth can be accurately transferred to a number of tubes by a downward action of the syringe plunger.

BRIEF DESCRIPTION OF THE DRAWINGS

A more complete appreciation of the invention and many of the attendant advantages thereof will be more readily apparent as the same becomes better understood by reference to the following detailed description when considered in connection with the accompanying drawings wherein.

DETAILED DESCRIPTION

Figure 1:
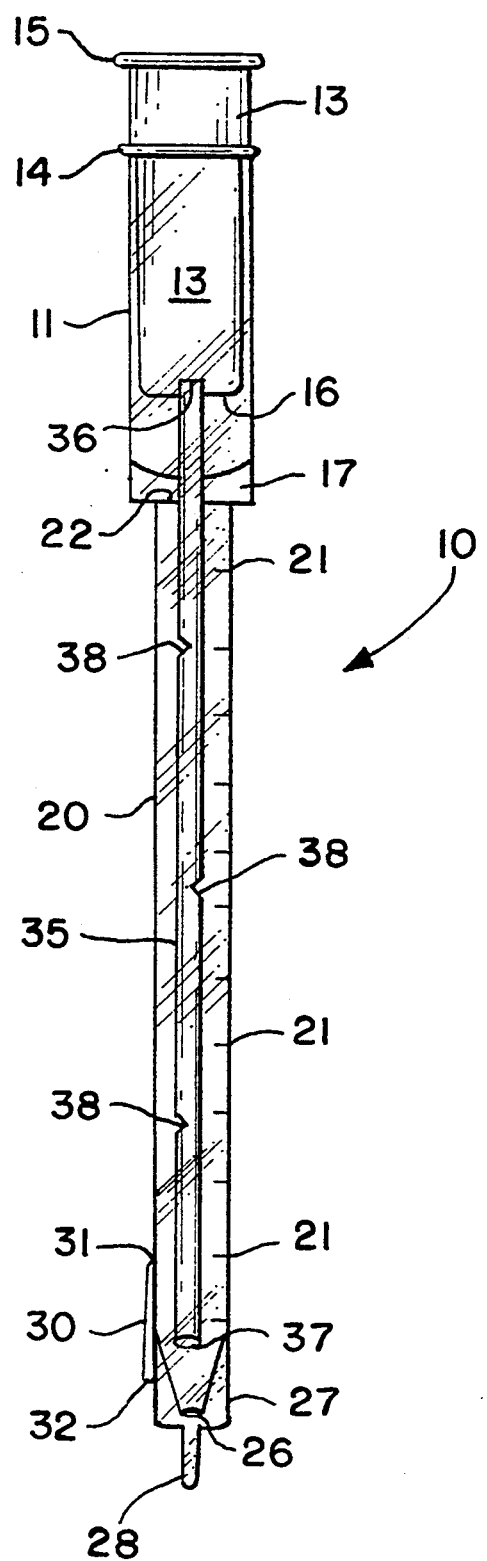
FIG. 1 is a part schematic view of a disposable pipette-syringe-tubular sampling probe combination according to the present invention.

Referring now to the drawings and more particularly to FIG. 1, there is shown a part schematic view of the preferred embodiment of a disposable pipette-syringe-tubular sampling probe combination, according to the present invention and designated generally by reference numeral 10. A first end of pipette 10 is formed of an elongated syringe barrel 11 having a plunger 13 slidably disposed therein. One end of barrel 11 is provided with an external bead 14 and serving to limit the movement of plunger 13 therein.

Plunger 13 is provided with a beaded end 15 that engages bead 14 on barrel 11 when the plunger is fully depressed. The other end of plunger 13 is provided with a rounded end 16 that engages the bottom 17 of barrel 11 when the plunger is fully depressed. An elongated, hollow, pipette tube 20, having graduated indicia 21 thereon, has one end secured in fluid communication with an opening 22 in the bottom 17 of barrel 11.

Pipette tube 20 is provided with a tapered tip terminating in an orifice 26. A removable, plastic, protective cover 27 is disposed over orifice 26 and extends over a portion of the length of tube 20. An elastomeric strap 30 is attached at one end to the exterior of pipette tube 20, as designated by reference numeral 31. The other end of elastomeric strap 30 is secured to an edge surface of removable cover 27, as designated by reference numeral 32. Elastomeric strap 30 is under tension when orifice cover 27 is disposed over pipette orifice 26, as illustrated in FIG. 1. An extension tab 28 is provided on the end of removable cover 27 to permit manual grasping thereof for manual removal and replacement of cover 27 over orifice 26, as will be further explained hereinafter.

An elongated tubular sampling probe 35 having an end 36, secured to and closed by, the rounded end 16 of plunger 13 extends through opening 22 and along the internal hollow portion of pipette tube 20. The length of tubular sampling probe 35 is selected such that the unattached, or free, open tip end 37 thereof is maintained within the pipette tube 20 when plunger 13 is partially retracted, and is extended a controlled distance from pipette tube orifice 26, when plunger 13 is fully depressed, or when rounded end 16 thereof is in engagement with bottom 17 of barrel 11. A plurality of transverse openings 38 are provided at staggered locations through the sidewall of tubular sampling probe 35 and at spaced intervals along the length thereof, and the function of which will be further explained hereinafter.

Figure 2:
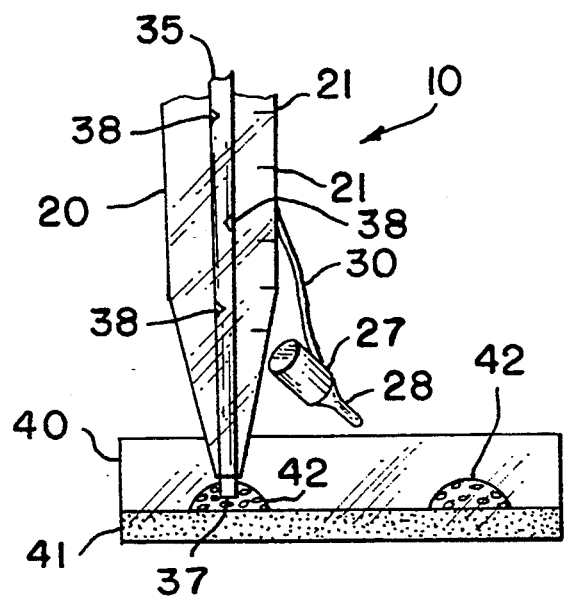
FIG. 2 is an enlarged view of the tip end of the pipette-syringe-tubular sampling probe combination shown in FIG. 1, showing the elastomeric retraction of the orifice cover from the pipette orifice; and illustrating direct sampling by the tubular sampling probe from a colony growth in a Petri dish.

Referring now more particularly to FIG. 2, protective cover 27 has been moved away from its orifice covering position. Tubular sampling probe 35 is shown depressed (via movement of plunger 13) sufficiently for open end 37 thereof to have engaged and moved cover 27 away from its orifice covering position. Protective cover 27 is frictionally disposed on pipette tube 20 but is removable therefrom by the force of tubular sampling probe 35 acting against the interior bottom surface thereof or manually removed by grasping extension tab 28 and exerting a pulling force thereon.

A Petri dish 40, having a quantity of nutrient agar 51 supporting culture growth for colonies 52 thereon, is shown in FIG. 2. After removal of cover 27 from orifice 26, tubular sampling probe 35 is extended via action of plunger 13 and a portion of tip 37 touched or embedded within surface colony 52 within Petri dish 40. As tubular sampling probe 35 is touched or embedded within culture colony 52, cells are collected in and around the lumen of the tube opening 37.

Figure 3:
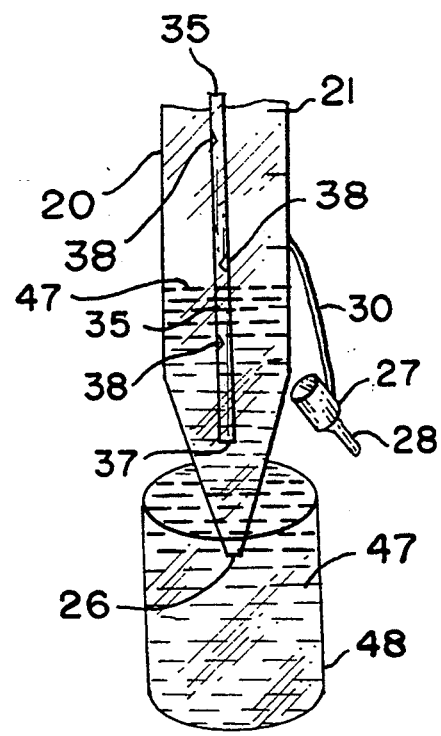
FIG. 3 is a part schematic illustration of the pipette structure shown in FIG. 2 when extracting a quantity of growth medium from a container of nutrient broth.

Referring to FIG. 3, after tubular sampling probe 35 is retracted from culture growth 42 (FIG. 2) back inside of pipette tube 20, the open end of pipette tube 26 is immersed in sterile nutrient broth 47 housed in container 48. Further withdrawal of plunger 13 in syringe barrel 11 extracts a quantity of nutrient broth 47 from container 48 into pipette tube 20. The force of nutrient broth 47 moving into pipette tube 20 causes adhered cells on and within tubular sampling probe 35 to be freed and moved into the lumen of tubular sampling tube 35. Transverse openings 38 in the sidewall of tubular sampling probe 35 permits bacterial cells inside tubular probe 35 to mix with the nutrient broth 47 surrounding the tube and establish areas of growth. After the desired quantity of nutrient broth is received within pipette tube 20, as indicated by the indicia 21 thereon, protective cover 27 is manually placed over pipette orifice 26, utilizing extension tab 28, to hermetically seal the end of pipette tube 20. Plastic cover 27 is designed to stretch fit over pipette tube 20 for hermetically sealing thereof.

Protective cover 27 may also be provided with internally and circumferentially disposed ribbed surfaces to act as 0-ring seals to assist in maintaining the hermetically sealed condition between the cover and pipette tube end, if so desired. The bottom surface of cover 27 is constructed such that puncture thereof, by the blunt end 37 of tubular sampling probe 35, is prevented upon removal thereof by probe 35.

Figure 4:
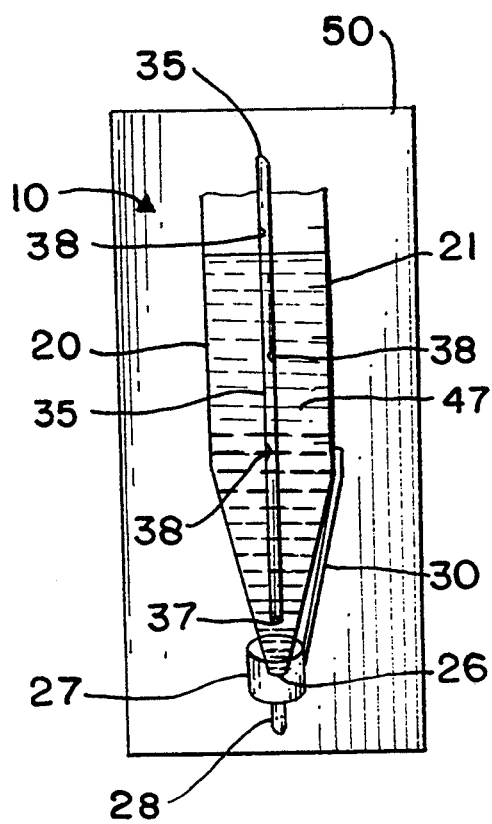
FIG. 4 is a part schematic view of the orifice covered pipette structure shown in FIGS. 1-3 containing a quantity of nutrient broth sealed therein by the orifice cover and disposed within an incubator for additional colony growth.

After sealing the quantity of nutrient broth 47 within pipette tube 20, the entire pipette 10 is placed within a suitable incubator 50 (FIG. 4) for 18-24 hours at 37 degrees C. After incubation, the accumulated growth is uniformly distributed by a back-and-forth rocking motion of pipette 10. After again removing protective cover 27, the growth can be accurately transferred to a number of tubes by a downward movement of syringe plunger 13.

Figure 5:
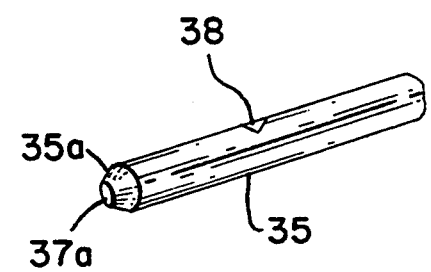
FIG. 5 is a part schematic view of a modified tip end portion for the tubular sampling probe shown in FIGS. 1-4.

Referring now more particularly to FIG. 5, a modified tubular sampling component probe 35 is illustrated and provided with a biased or tapered sharp point tip opening, as designated by reference numeral 37a. Although the blunt, or horizontal end 37 on elongated probe 35, as illustrated in FIGS. 1-4, is specifically designed for recovering cells from an agar surface colony, it works equally as well for recovering cells in a liquid environment (surface or submerged), or growth in a more viscous medium, such as soft agar.

Modification of the distal end of tubular probe 35 permits penetration of solid or semi-solid materials as described herein. The tip end 37a of tubular probe 35 is formed or machined to produce a sidewall cutting opening by means of a bevelled edge 35a that encircles the tube opening (FIG. 5). This bevelled configuration is an adaptation of a laboratory cork borer used to produce holes or openings in cork or rubber stoppers.

Figure 6:
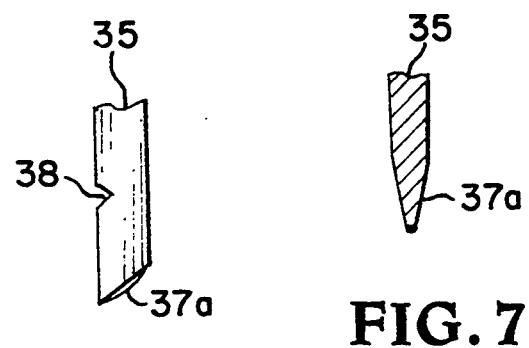
FIG. 6 is a part schematic view of another modified tip end portion for the tubular sampling probe shown in FIGS. 1-4.
Figure 7:
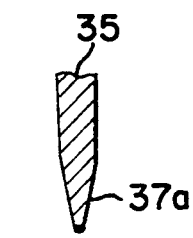
FIG. 7 is a schematic, part sectional enlarged view of a portion of the tip end of the modified tubular sampling probe shown in FIG. 6.

The tip end portion 37a of tubular probe 35 is formed, or machined, to taper on one (FIG. 5) or both surfaces (FIGS. 6 and 7) from the normal cross-sectional tubular wall thickness to a sharp leading edge to assist in penetrating solid or semi-solid materials for the recovery of microorganisms. The sharp point on tip 37a on the distal end of tubular probe 35 (FIGS. 5, 6, and 7) further facilitates penetration of these solid or semi-solid materials, when needed, for example, in the course of postmortem examinations in human and veterinary medicine where a microbial infection is suspected. By providing sharp end points 37a to the blunt end of tubular probe 35, the probe can function equally well in sampling "agar" colonies or penetrating solid or semi-solid materials, as well as also finding utility in the food industry when taking samples of meat, poultry, and dairy (cheese) products.

Obviously, when employing a tubular sampling probe 35 in each of these situations, the amount of material collected inside and on the tube will be greater than that obtainable by a straight wire or loop, as previously employed for these purposes. This increase in sample material greatly improves the probability of detecting contamination, especially in situations of low cell counts. When employing the tapered or biased tip 37a (FIG. 6) for collecting samples from agar growth of the type shown in FIG. 2, the pipette 10 would be disposed at an angle to maximize contact of the tapered open tip 37a with the colony growth.

It is thus seen that tubular sampling probe 35 and its transverse openings 38 provides more efficient collection and dispersal of cells within pipette 10 than that achieved by the solid wire probes as employed in previous applications. Also, subsequent bacterial growth after incubation is more uniform and total growth is obtained in shorter periods of time than that achieved by solid wire probes.

Tubular sampling probe 35 may be constructed of suitable plastic or metal tubing. Laboratory quality clear or translucent plastic, such as polyvinyl chloride, polyethylene or other rigid plastic materials are suitable for constructing tubular sampling probe 35. Also, suitable aluminum, brass and other metal tubing, in diverse diameters and suitable for constructing tubular sampling probe 35, is available from K & S Company of Chicago, Ill., and others. In a specific example of the present invention, 1/16" (0.0625") brass tubing was employed for tubular sampling probe 35, and openings 38 were provided therein at approximately one inch spaced relationship, and in a staggered or alternate 180° array. The particular number and orientation of the openings is not considered critical, although at least one opening should be in reasonably spaced adjacency to opening 37 of probe 35.

In the specific embodiment described, openings 38 were formed as notches filed through the sidewall of tubular probe 35. Suitable high speed drills could also be employed to provide any suitable number of such openings in probe 35, as so desired, the important criteria being that adequate opening space be provided to ensure disbursement, and growth media flow, within tubular sampling probe 35 to promote complete growth of all sample culture obtained within the tubular probe. In the specific embodiment described, tubular sampling probe 35 was inserted into a 1/16" hole drilled into the rounded end 16 of plunger and sealed in fixed position therein by a conventional adhesive, ("Krazy Glue") to provide closed end 36. The length of tubular sampling probe 35 is sufficient to provide an extension of open end 37 at least one-half inch beyond pipette orifice 26 when tube 35 is extended by complete depression of syringe plunger 13 within syringe barrel 11.

Most of the remaining component parts of the present invention are formed of conventional clear or translucent plastic such as polyvinylchloride, polyethylene or other rigid plastic. Elastomeric strap 30 in the preferred embodiment is formed of a conventional rubber band, of suitable size and resiliency, to be stressed while cover 27 is covering orifice 26 and to retract the covers to the side of pipette tube 20 when removed from their covering position. Any conventional bonding or adhesive material, such as commercially available "super glue", may be employed to attach the ends of elastomeric strap 30 to pipette tube 20 and to protective cover 27 prior to packaging and sterilizing of pipette 10. Pipette 10 may be any of various conventional sizes and the entire pipette is a disposable unit intended to be delivered to the site of use in a sterile condition and adapted for "only-one-use".

The specific embodiments of the invention described herein are intended to be illustrative only and are therefore not to be deemed as exhaustive. There are numerous modifications and variations of the invention that will be readily apparent to those skilled in the art in the light of the above teachings. For example, elastomeric strap 30 is not essential to the operation of the tubular sampling probe and, in some instances, may be omitted.

Other changes and modifications of the specific embodiments disclosed herein will be apparent to those skilled in the art. It therefore to be understood that, within the scope of the appended claims, the invention may be practiced other than as specifically described herein.

What is claimed as new and desired to be secured by Letters Patent of the United States is:

1. A microbial retrieval and sampling device including:
   an elongated pipette having a first and a second end;
   a syringe including a barrel containing a slidable plunger provided at said first end of said pipette;
   a pipette orifice formed at the second end of said pipette;
   an elongated tubular sampling probe having a closed end secured to said slidable plunger and an open free end disposed adjacent said pipette orifice;
   said elongated tubular sampling probe being movable with said slidable plunger between a first position wherein said open free end thereof is disposed within said pipette and a second position wherein said open free end of said tubular sampling probe extends exteriorly of said pipette orifice;

removable cover means exteriorly disposed over said pipette orifice;

said removable cover means being manually and slidably removable to expose said pipette orifice to expose said pipette orifice to permit said tubular sampling probe to be extended from said pipette orifice under the influence of said slidable plunger;

said tubular sampling probe including an annular sidewall;

at least one transverse opening in said annular sidewall of said tubular sampling probe, and wherein said at least one transverse opening in said annular sidewall of said tubular sampling probe is disposed in spaced adjacency to said open free end of said tubular sampling probe.

2. The microbial retrieval and sampling device of claim 1 wherein the portion of said elongated tubular sampling probe forming said open free end is provided with an exterior bevelled surface leading to a sharp end edge.

3. The microbial retrieval and sampling device of claim 1 including multiple transverse openings in said annular sidewall of said tubular sampling probe, said multiple transverse openings being disposed in spaced relationship along the length of said tubular sampling probe.

4. The microbial retrieval and sampling device of claim 3 wherein said tubular sampling probe is selected from tubular metals and tubular plastics and wherein said transverse openings are selected from circular bores and notches formed in said annular sidewall of said tubular sampling probe.

5. The microbial retrieval and sampling device of claim 1 wherein the portion of said elongated tubular sampling probe forming said open free end is provided with a cross sectional wall thickness tapering to a razor sharp end edge.

6. The microbial retrieval and sampling device of claim 1 wherein said open free end of said elongated tubular sampling probe is selected from a group of opening configurations consisting of (a) a biased or tapered opening and (b) a horizontal or perpendicular opening, relative to the length of said elongated tubular sampling probe.

7. A microbial retrieval and sampling device including:

an elongated pipette having a first and a second end;

a pipette orifice formed at the second end of said pipette;

a syringe structure having a barrel containing a slidable plunger forming said first end of said elongated pipette;

an elongated tubular sampling probe having a closed end secured to said slidable plunger and an unattached open end disposed adjacent said pipette orifice;

said tubular sampling probe including an annular sidewall;

at least one transverse opening provided through said annular sidewall of said tubular sampling probe;

said at least one transverse opening being disposed in spaced adjacency to said open unattached end of said tubular sampling probe;

said slidable plunger serving to move said elongated tubular sampling probe between a first position wherein said unattached open end is disposed within said pipette and a second position wherein said unattached open end extends exteriorly of said pipette orifice for contact and sampling of a microbial culture;

manually removable cover means connected to said pipette and disposed over said pipette orifice; whereby said manually removable cover means being removed from over said pipette orifice to permit said open end of said elongated tubular sampling probe to be moved into contact with and take a sample from the microbial culture and when said elongated tubular sampling probe is retracted to said first position within said pipette, a sterile nutrient broth being added to said pipette and sealed therein by manually replacing said removable cover means, the nutrient broth will contact the sample taken by said tubular sampling probe at said pipette orifice at said second end as well as through said at least one transverse opening in said annular sidewall thereof.

8. The microbial retrieval and sampling device of claim 7 wherein said unattached open end of said elongated tubular sampling probe is provided with a uniform wall thickness over a major portion of the length thereof and provided with a bevelled exterior portion at said unattached open end that terminates in a razor sharp end edge.

9. The microbial retrieval and sampling device of claim 8 wherein a plurality of transverse openings are provided in spaced relationship through said annular sidewall of said tubular sampling probe, said plurality of transverse openings being selected from circular bores and notches formed in said annular sidewall of said tubular sampling probe.

10. The microbial retrieval and sampling device of claim 9 wherein said tubular sampling probe is selected from tubular metal and tubular plastic materials.

11. The microbial retrieval and sampling device of claim 7 wherein said tubular sampling probe is a tubular metal selected from the group of tubular metals consisting of aluminum and brass and said at least one transverse opening provided through said annular sidewall of said tubular sampling probe comprises a plurality of transverse openings disposed in spaced relationship from each other and disposed in a staggered array with each of said plurality of transverse openings being disposed 180 degrees relative to a next adjacent transverse opening along the length of said tubular sampling probe.

12. The microbial retrieval and sampling device of claim 7 wherein said elongated tubular sampling probe is provided with a uniform wall thickness over a major portion of the length thereof and provided with a tapering cross sectional wall area at said unattached open end that tapers to a razor sharp end edge.

13. The microbial retrieval and sampling device of claim 7 wherein said unattached open end of said elongated tubular sampling probe is selected from the group of openings consisting of (a) a biased or tapered opening and (b) a horizontal or perpendicular opening, relative to the length of said elongated tubular sampling probe.

* * * * *